United States Patent [19]

Page, Jr. et al.

[11] 4,040,311
[45] Aug. 9, 1977

[54] DENTAL HANDPIECE

[75] Inventors: Joe W. Page, Jr., Huntington Beach; Paul H. Stahlhuth, Mission Viejo, both of Calif.

[73] Assignee: Joe W. Page, Jr., Huntington Beach, Calif.

[21] Appl. No.: 646,069

[22] Filed: Jan. 2, 1976

Related U.S. Application Data

[63] Continuation-in-part of Ser. No. 477,803, June 10, 1974, Pat. No. 3,942,392.

[51] Int. Cl.² ............................................... F16H 3/44
[52] U.S. Cl. .................... 74/750 R; 415/503; 32/56; 32/59
[58] Field of Search ............ 74/750 R; 415/503; 418/266, 270; 32/40 R, 53, 56, 58, 59, DIG. 1, 28

[56] References Cited

U.S. PATENT DOCUMENTS

| 660,411 | 10/1900 | Blum | 32/56 |
|---|---|---|---|
| 2,251,057 | 7/1941 | Iseman | 32/DIG. 1 |
| 3,832,088 | 11/1974 | Cromie | 415/503 X |
| 3,942,392 | 3/1976 | Page, Jr. et al. | 74/750 R |

Primary Examiner—Samuel Scott
Assistant Examiner—Don E. Ferrell
Attorney, Agent, or Firm—Fred N. Schwend

[57] ABSTRACT

A straight dental handpiece comprising a pair of telescoping housing barrels which can normally swivel relative to each other, one containing a chuck and the other containing a vane type air motor. A change speed transmission is entrained between the motor and the chuck, such transmission being adjustable to change speeds by relative endwise movement of the barrels. Opening and closing of the chuck is accomplished by relative rotation of the barrels while holding down a stop button. A reversing valve, also on the handpiece, is movable into either of two positions relative to one of the barrels to supply air under pressure to either of two passages to drive the motor in one direction or the other.

15 Claims, 7 Drawing Figures

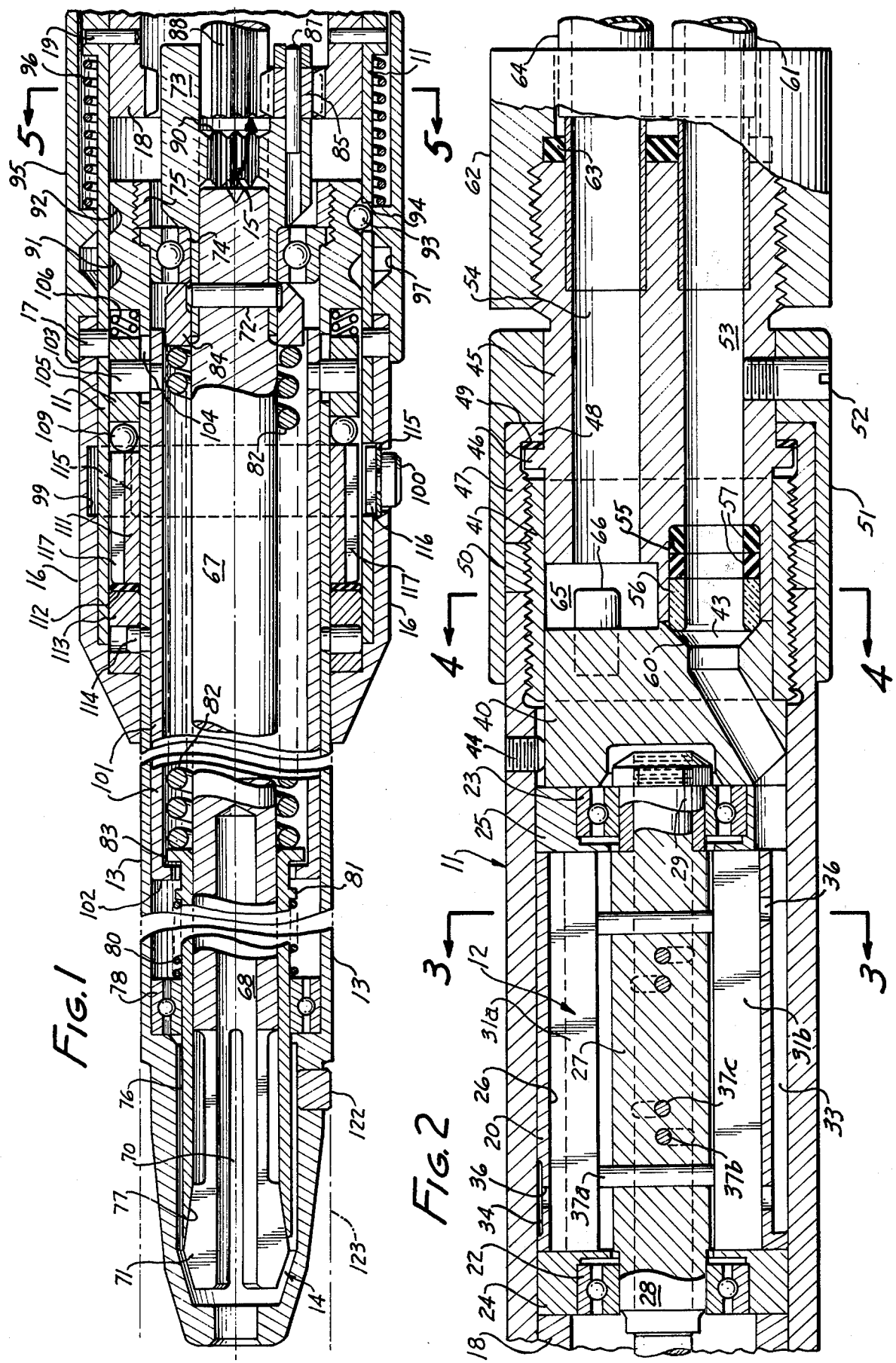

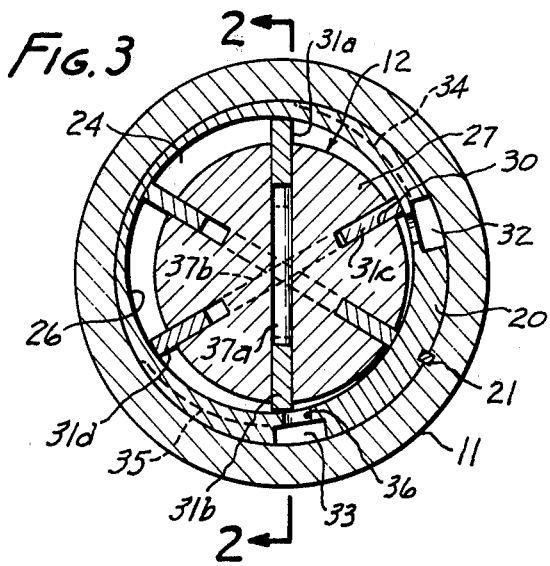
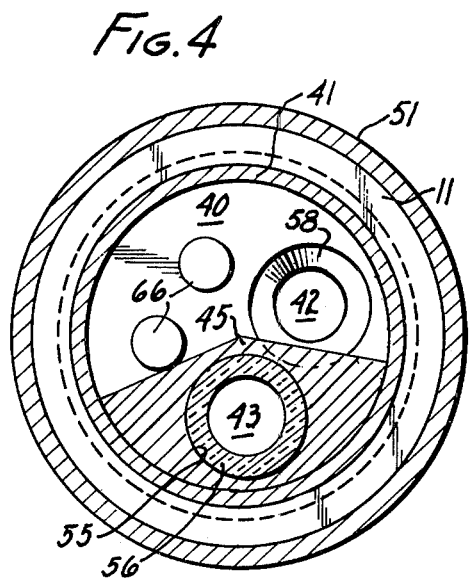
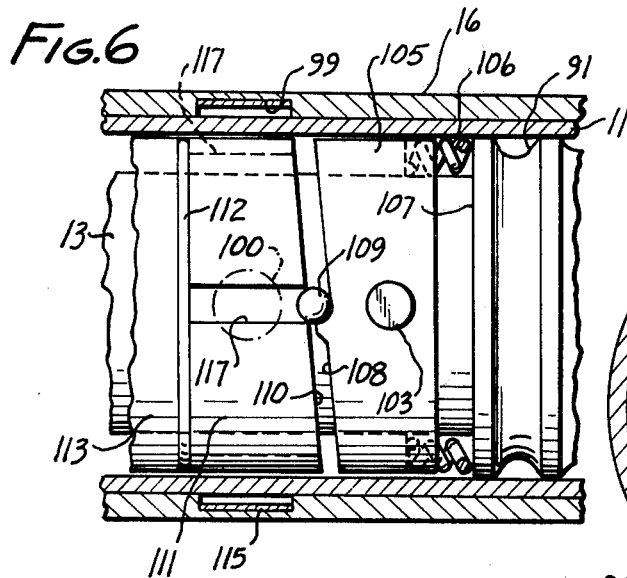
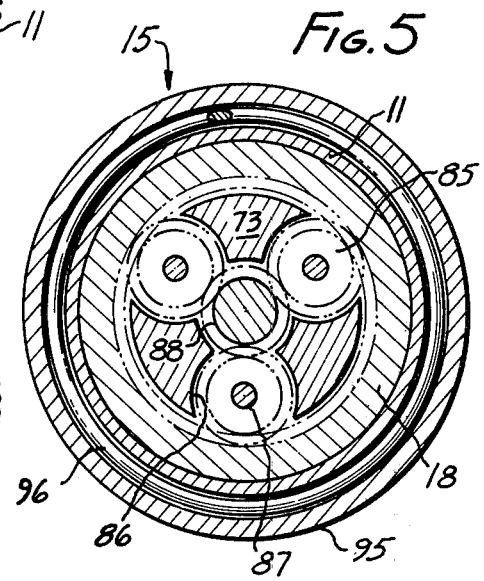
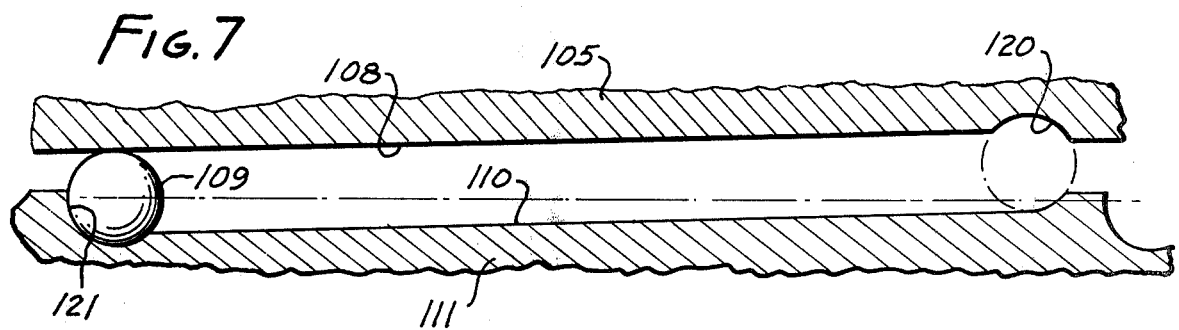

DENTAL HANDPIECE

This is a continuation-in-part of our pending application, Ser. No. 477,803, filed June 10, 1974 now U.S. Pat. No. 3,942,392.

BACKGROUND OF THE INVENTION

1. Field of the Invention

This invention relates to fluid driven dental handpieces, particularly of the straight type.

2. Description of the Prior Art

Modern dental handpieces of the above type generally comprise a chuck which is powered by an air driven motor located in the handpiece itself. Turbine motors are not generally satisfactory for straight type handpieces since they operate most efficiently at high speeds, on the order of 250,000 rpm or more and have relatively low torque. The speed of the turbine can be reduced by throttling the supply of air applied thereto under pressure, but in doing so, the torque is further reduced.

For certain types of dental work, it is often desirable to operate the handpiece at a relatively lower speed and at higher torque. For example, it is found that certain tooth cleaning, drilling and other operations are best performed at speeds on the order of 5,000 rpm whereas certain polishing operations are better performed at somewhat higher speeds, on the order of 15,000 to 25,000 rpm.

In our aforementioned patent application Ser. No. 477,803, we describe and claim a dental handpiece comprising two telescoping barrels, one carrying a vane type motor and the other carrying a chuck. A two speed transmission is provided to transmit rotation from the motor to the chuck and the barrels are movable axially relative to each other to shift the transmission from one speed setting to the other. This works quite satisfactory.

Such dental handpieces are very compact and must be easy and convenient for a dentist to manipulate. This imposes severe design problems since projecting controls for opening and closing the chuck, changing speeds, reversing direction of rotation, etc., must be kept to a minimum and must not interfere with proper operation of the handpiece or convenience in handling the same. Also, it is highly desirable for the barrels to normally freely swivel relative to each other so that the flexible power conduit, such as an air hose, for supplying power to the handpiece does not hinder manipulation of the part or barrel of the handpiece which is normally held by the dentist. Further, such handpieces must provide for ready attachment of the usual contra-angle tips or other tools thereto.

Although the handpiece of our above noted patent application Ser. No. 477,803 provided for the attachment of such contra-angle tips, the chuck moved axially a small amount relative to the forward barrel during opening and closing of the chuck and this tended to make it difficult to properly attach certain contra-angle tips thereto.

STATEMENT OF THE INVENTION

A principal object of the present invention is to provide a dental handpiece having a readily adjustable change speed transmission and chuck opening and closing feature, both controlled by relative movement of two housing barrels, while permitting the barrels to normally freely swivel relative to each other.

Another object is to provide a chuck opening and closing device for a dental handpiece which may be opened and closed with a minimum amount of effort and without requiring tools.

Another object is to provide a dental handpiece of the above type which may be readily and easily attached to a contra-angle tip or other dental tool.

Another object is to reduce the wear of the vanes and cylinder walls of a vane type motor in dental handpieces.

A further object is to reduce the tendency of vanes of a vane type motor to stick within their slots, thus causing erratic starting.

The manner in which the above and other objects of the invention are accomplished will be readily understood on reference to the following specification when read in conjunction with the accompanying drawings.

BRIEF DESCRIPTION OF THE DRAWINGS

FIGS. 1 and 2 jointly form a longitudinal sectional view through a straight dental handpiece embodying the present invention and illustrate the same in a slow speed setting.

FIG. 3 is a transverse sectional view taken along the line 3—3 of FIG. 2, illustrating the air driven motor.

FIG. 4 is a transverse sectional view taken along the line 4—4 of FIG. 2, illustrating part of the reversing controls for the air driven motor.

FIG. 5 is a transverse sectional view taken along the line 5—5 of FIG. 1, illustrating the planetary gear drive system.

FIG. 6 is a fragmentary longitudinal sectional view, with parts shown in full outline, showing the camming means for opening the chuck.

FIG. 7 is a developed view of the camming means shown in FIG. 6 for opening the chuck.

DESCRIPTION OF THE PREFERRED EMBODIMENT

In general, the handpiece comprises a rear housing barrel 11 containing a vane type air motor generally indicated at 12, and a forward inner housing barrel 13 slideable and rotatable within the rear housing barrel 11 and containing a chuck or collet generally indicated at 14. A change speed transmission generally indicated at 15 is connected intermediate the motor 12 and chuck 14 to enable the speed of the chuck drive to be changed from a high speed 1 to 1 ratio, i.e., a direct drive, to a low speed 1 to 4 ratio.

More specifically, the rear barrel 11 has a counter-bored nose piece 16 secured to the forward end thereof by pins 17. A ring gear 18, forming part of the transmission unit 15, is secured within the barrel 11 by pins 19.

An air motor cylinder or stator 20, FIGS. 2 and 3, is also secured within the barrel by a key 21 and is located between two ball bearings 22 and 23 which are fitted within bearing housings 24 and 25, respectively, suitably secured within the barrel 11 at opposite ends of the cylinder 20.

The cylinder 20 has a bore 26 therein whose axis is eccentric to the coincident axes of the barrel 11 and the bearings 22 and 23. A rotor 27 is rotatable within the bore 26 and has trunnion bearing portions 28 and 29 supported for rotation within the bearings 22 and 23, respectively.

The outer periphery of the rotor 27 is concentric with the axes of the bearings 22 and 23 and six equi-angularly spaced radially extending slots 30 are formed along the length thereof to slideably receive vanes 31 adapted to slide radially within the slots.

In order to convey air to and from the motor 12 to drive the same in either direction, two longitudinally extending passages 32 and 33 are formed lengthwise along a part of the length of the cylinder 20 and are located approximately 120° apart, as viewed in FIG. 3. Parts of such passages also extend circumferentially approximately 60° as indicated at 34 and 35, and small holes 36 are formed in the wall of cylinder 20 intermediate the passages 32, 33 and bore 26 of the cylinder 20 to convey air under pressure to one side of the rotor 24 and to exhaust the air from the other side of the rotor during driving of the latter in either direction.

According to one aspect of the invention, and in order to substantially eliminate sticking of the vanes 31 in the slots 30 of the rotor 27, which could otherwise eliminate or reduce the available starting torque, the pairs of diametrically opposed vanes 31 are held to a minimum total diametrical dimension by pairs of spaced pins 37a, 37b and 37c slidably mounted within bearing holes formed radially through the rotor 27. For example, diametrically opposed vanes 31a and 31b are integrally connected by a pair of spaced pins 37a while vanes 31c and 31d are integrally connected by a pair of spaced pins 37b which are spaced axially from the pins 37a, etc. Thus, the diametrically opposed vanes of each pair slide in unison radially of the rotor during rotation of the latter, one being moved outwardly by the other as the latter is cammed inwardly by the inner bore surface 26. Accordingly, the vanes are held in close proximity to the cylinder bore independently of centrifugal force to provide sufficient sealing and thus insure adequate and consistent starting torque. Pins 37a, etc., also maintain a close running clearance between the vanes 31 and the bore 26 when starting and at all other times.

In order to introduce air under pressure to either of the passages 32 and 33, to determine the direction of rotation of the rotor 27, and to exhaust such air through the other passage, a valve plate 40 is maintained in intimate contact with the bearing housing 25 by a coupling sleeve 41 screw threaded within the right hand end of the barrel 11. A pair of openings 42 and 43, see FIG. 4, are formed in the valve plate 40 and these communicate with respective ones of the passages 32 and 33.

A lock screw 44 locks the valve plate 40 in properly oriented position.

A valve member 45 having an annular flange 46 thereon is rotatably mounted within the sleeve 41 and is retained against axial movement by a retainer nut 47 screw threaded on the sleeve 41 and provided with an inwardly extending annular lip 48 which holds a sealing ring 49 against the flange 46.

A lock nut 50 is threaded on the sleeve 41 to lock the retainer nut 47 in properly adjusted position. Also, a sleeve 51 is secured to the valve member 45 by a lock screw 52 to facilitate manual rotation of the valve member.

The valve member 45 is provided with an air inlet passage 53 and an air exhaust passage 54 extending longitudinally therethrough. The inlet passage 53 leads to a counterbore 55 in which a plastic sleeve 56 is slideably mounted and urged forwardly by a pair of resilient rings 57 of elastomeric material, causing the sleeve 56 to normally seat in one of two chamfered shoulders 58 and 60, see also FIG. 4, surrounding the passages 42 and 43, respectively, in the valve plate 40, depending on the rotated position of the valve member 45, thereby providing an effective seal against air leakage.

The inlet passage 53 leads rearwardly to a flexible inlet conduit 61 connected to a suitable air pump or other supply of air under pressure, not shown, and is coupled to the valve member 45 by a cap 62 which is threaded on the valve member and is compressed against an elastomeric disk 63 fitted over the conduit 61 and over a second flexible exhaust conduit 64 communicating with the exhaust passage 54. The conduit 64 preferably leads to a suitable sound muffling device, not shown, located remotely from the handpiece so that any noise generated or conducted by the air passing through the air motor 12 will not disturb the dentist or the patient. The passage 54 terminates forwardly in a compartment 65 formed at the forward end of the valve member 45 and communicating with one of the passages 42 and 43 in the valve plate 40, depending on the rotated position of the valve member 45.

By rotating the valve member 45 through approximately 120°, the inlet passage 53 may be connected to either passage 42 or 43, and in either position, engagement of the sleeve 56 with the chamfered surface 58 or 60 will act to both seal the connection and to detent the valve member in position. Stop pins 66 extend from the valve plate 40 to limit rotation of the valve member 45 to either of its alternate positions.

From the foregoing it will be seen that when the valve member 45 is set in its position illustrated in FIG. 2, air under pressure is transmitted through passages 53, 43, 33, and holes 36 to exert pressure against the adjacent two or three vanes 31, causing a clockwise rotation of the motor, as viewed in FIG. 3. The exhaust air carried around the periphery of the rotor by the vanes is exhausted through the holes 36 in the opposite passage 32 from whence it is conveyed through passages 42, 54 and is exhausted through the conduit 64. By rotating the valve member 45 through 120°, the inlet passage 53 will be aligned with the passage 42 in the valve plate 40, enabling the pressured air to cause rotation of the rotor 27 in a counterclockwise direction, in which case the exhausted air will pass through passage 33 and chamber 65 into the exhaust passage 54.

Describing now the chuck 14 and change speed transmission 15, the chuck is formed on the forward end of a chuck shaft 67 which has an axial hole 68 therein to receive a dental burr or the like and is slotted at 70 to form four radially flexible chuck fingers 71.

The shaft 67 is pinned at 72 to a planetary gear carrier 73 which is rotatably supported by a ball bearing 74 fitted within the forward housing barrel 13. An annular clamp nut 75 is threaded in the barrel 13 preventing endwise movement of the bearing 74 and chuck shaft 67 relative to the barrel 13.

A chuck closing sleeve 76 having an inner conical camming surface 77 at the forward end thereof engageable with mating surfaces on the clutch fingers 71, is slideably fitted over the chuck shaft 67 and, in turn, is slideably fitted within a ball bearing 78 which is mounted within the forward end of the barrel 13. A light compression spring 80 is compressed between the inner race of the bearing 78 and a flange 81 on the sleeve 76 to hold the bearing in place and to provide a predetermined preload thereon. A second relatively heavy spring 82 is mounted over the shaft 67 and is compressed between a flange 83 on sleeve 76 and a keeper ring 84 engaging the inner race of bearing 74. Thus, the spring 82 is effective to force the sleeve 76 to cam the clutch fingers 71 inwardly into their illustrated clutch closing positions. Opening of the clutch will be described later.

The drive transmission 15 comprises three planetary gears 85, FIGS. 1 and 5, rotatable within openings 86 formed in the carrier 73 and rotatably mounted on pins 87 extending in the carrier. When the forward barrel 13 is located in its forward relative position shown in FIG. 1, the planetary gears 85 mesh with both the ring gear 18 and a sun gear 88 formed on the forward end of the rotor 27. Accordingly, rotation of the rotor 27 and sun gear 88 will cause the planetary gears 85 to revolve about their axes and in mesh with the stationary ring gear 18, causing the carrier 73 and chuck 14 to rotate at a relatively low speed, the gear ratios being such that the chuck will rotate at ¼ the speed of the rotor 27. When the barrel 13 is slid to a rearward position in the manner to be described presently, the planetary gears 85 are moved endwise out of mesh with the ring gear 18 but will remain in mesh with the sun gear 88. At this time, the sun gear will engage spline teeth 90 on the planetary carrier 73 to form a direct coupling between the rotor 27 and the chuck.

For the purpose of normally enabling free swiveling of the rear barrel 11 and/or telescoping movement of the forward barrel 13 within the rear barrel, and for locking the barrels in either of two telescoped positions, the forward barrel 13 is provided at its rear end with two axially spaced circumferential grooves 91 and 92 engageable by balls 93 movable transversely through holes 94 in the wall of barrel 11 and normally retained in their locking positions shown in FIG. 1 by a locking ring 95. The latter is slideably mounted on the rear barrel 11 and is normally held in its illustrated locking position by a compression spring 96 to hold the balls 93 partly in holes 94 and partly in one of the grooves 91 and 92, permitting free relative swiveling between the barrels in either telescoped positions thereof.

The locking ring 95 is provided with an inner circumferential groove 97, and when the ring 95 is shifted rearward, groove 97 is aligned with the balls 93, permitting them to move outwardly in holes 94, thereby freeing the forward barrel 13 to be shifted rearwardly from its position shown in FIG. 1 to its alternate position wherein the balls 93 can engage in the groove 91.

In order to open the chuck 14, a button 100, FIG. 1, is held depressed to lock a cam sleeve 111 to the barrel 11 and the barrels 11 and 13 are rotated relative to each other, causing rearward sliding movement of the chuck closing sleeve 76 to permit the clutch fingers 71 to spring apart sufficiently to free any dental tool they may be gripping. For this purpose, a sleeve 101 is slideably fitted within the barrel 13 and has an inwardly extending flange 102 overlapping the flange 83 of the sleeve 76. Sleeve 101 is attached to pins 103 slideable along elongated slots 104 extending endwise in the wall of barrel 13. The pins 103 are also attached to a cam sleeve 104, see also FIG. 6, which is slideable endwise on the barrel 11 and urged toward its illustrated forward position by compression springs 106 extending between the sleeve 105 and a shoulder 107 formed on the barrel 13.

As seen in FIGS. 6 and 7, the sleeve 105 has a cam surface 108 on the forward end thereof which engages a pair of diametrically arranged balls 109 riding on a similar cam surface 110 formed on the rear end of the second cam sleeve 111 which is rotatably mounted on the forward barrel 13. Sleeve 111 bears against a thrust washer 112 of anti-friction material such as tetrafluorethylene which, in turn, bears against a ring 113 secured to the forward barrel 13 by pins 114 and freely rotatable within the barrel 11.

The aforementioned stop button 100 projects through an opening in the wall of the barrel nose piece 16 and is mounted on the mid portion of an arcuate leaf spring 115 which is slideably mounted within an annular groove 99 formed in the nose piece 16. Spring 115 normally holds the button 100 in its outer illustrated position to maintain a stop lug 116 thereon out of engagement with the cam sleeve 111, thereby permitting the aforementioned free swiveling or rotation of the barrels 11 and 13 relative to each other. Longitudinally extending slots 117 are formed in the cam sleeve 111 around the periphery thereof.

When it is desired to open or close the chuck 14, the button 100 is depressed while rotating the barrels relative to each other to engage the stop lug 116 in an underlying slot 117 to lock the cam sleeve 111 to the barrel 11. Further movement of the barrels relative to each other will now cause relative rotation between the cam sleeves 105 and 111, causing the balls 109 to roll along the respective cam surfaces 108 and 110, forcing sleeve 105 rearwardly or allowing the springs 106 to move it forwardly depending on whether the barrels are rotated to open or close the chuck 14. If the barrels 11 and 13 are rotated to cam the sleeve 105 rearwardly, the flange 102 of slide 101 will pick up the clutch control sleeve 76, moving it rearwardly against the action of spring 82 to release the clutch fingers 71 so that they may open to permit removal or insertion of a burr or other workpiece in the axial hole 68. Thus, the balls 109 and one of the sleeves 105 and 111 form a cam follower means which follows the other sleeve.

As noted particularly in FIG. 7, the camming surface 108 for one of the balls 109 has a detent pocket 120 at one end of its slope and the opposite camming surface 110 for the same ball has a second detent pocket 121 at the opposite end of its slope. Accordingly, the balls 109 act through the sleeves 105 and 111 to detent the chuck 14 in either open or closed condition.

Due to the rolling action of the balls 121 along the relatively gradual slopes of their respective camming surfaces 108 and 110, little effort is required to compress the relatively heavy spring 82 to release the chuck 14.

A pin 122, FIG. 1, is secured to the forward end of the barrel 13 to orient a contra-angle or similar tool, partly indicated by dot-dash lines 123, on the forward end of the barrel 13.

It will be noted that because of the aforementioned structure, the chuck 14 will always remain in the same axial position relative to the barrel 13, even when being opened or closed so as to firmly anchor an attached contra-angle or other tool in place.

It will be obvious to those skilled in the art that many variations may be made in the exact structure shown without departing from the spirit of this invention.

We claim:
1. A dental handpiece comprising
a first housing barrel,
a second housing barrel movable axially in said first barrel between a first position and a second position,
a motor carried by one of said barrels,
a rotatable chuck carried by the other of said barrels,
a variable speed transmission mechanism intermediate said motor and said chuck, means responsive to movement of said second barrel axially relative to said first barrel to adjust said transmission to transmit rotation to said chuck at one speed and responsive to movement of said second barrel to said second position to adjust said transmission to transmit rotation to said chuck at another speed, and chuck control means responsive to relative rotation of said barrels in one direction to close said chuck and responsive to relative rotation of said barrels in the opposite direction to open said chuck.

2. A dental handpiece as defined in claim 1 wherein said chuck control means is effective to close and open said chuck when said second barrel is in said first position or said second position.

3. A dental handpiece as defined in claim 1 wherein said barrels are normally free to rotate relative to each other, and selectively actuable means effective when actuated and when said barrels are rotated relative to each other in one direction to cause said chuck control means to close said chuck.

4. A dental handpiece as defined in claim 3 wherein said selectively actuable means comprises a depressible push button carried by one of said barrels.

5. A dental handpiece as defined in claim 4 wherein said push button is effective when depressed and said barrels are rotated relative to each other in one direction to cause said chuck control means to close said chuck and when said barrels are rotated relative to each other in the opposite direction to cause said chuck control means to open said chuck.

6. A dental handpiece as defined in claim 1 wherein said chuck control means comprises a sleeve rotatably mounted on one of said barrels for rotation relative to both of said barrels,
a cam surface on said sleeve,
cam follower means for following said cam surface,
means controlled by said cam follower means for opening and closing said chuck, and
means for selectively coupling said sleeve to one of said barrels whereby relative rotation of said barrels will cause rotation of said sleeve relative to said cam follower means.

7. A dental handpiece as defined in claim 1 wherein said chuck control means comprises a sleeve rotatably mounted on one of said barrels,
said sleeve having a cam surface on one end thereof,
cam follower means for following said cam surface,
means controlled by said cam follower means for opening and closing said chuck,
means preventing relative rotation between one of said barrels and said cam follower means, and
means for selectively coupling said sleeve to the other of said barrels whereby relative rotation of said barrels will cause closing of said chuck.

8. A dental handpiece as defined in claim 1 wherein said chuck control means comprises a first sleeve rotatably mounted on one of said barrels,
said sleeve having a cam surface on one end thereof,
means for preventing axial movement of said sleeve,
a second sleeve slideable axially on said one barrel,
said second sleeve having a cam surface on the end thereof adjacent said first sleeve,
a roller element in rolling engagement with the cam surface of said first and second sleeves, means controlled by said second sleeve upon axial movement thereof for opening and closing said chuck, and
means for selectively coupling said first sleeve to the other of said barrels whereby relative rotation of said barrels will cause axial movement of said second sleeve.

9. A dental handpiece comprising
a first housing barrel,
a second housing barrel rotatably mounted in said first barrel,
a chuck supporting sleeve in said second barrel,
a bearing in said second barrel slideably and rotatably supporting said chuck sleeve,
a rotatable chuck slideably mounted in said chuck sleeve,
motor means for rotating said chuck,
said chuck having spring prongs for gripping a workpiece,
means for preventing axial movement of said chuck relative to said second barrel, and
means responsive to relative rotation of said barrels for moving said sleeve endwise in one direction to engage said prongs whereby to close said prongs.

10. A dental handpiece as defined in claim 9 wherein said last mentioned means comprises spring means for moving said sleeve endwise in one direction to close said prongs, and
means responsive to relative rotation of said barrels in one direction to enable said spring means to move said sleeve endwise in said one direction and responsive to relative rotation of said barrels in the opposite direction to move said sleeve in the opposite direction to enable said prongs to open.

11. A dental handpiece comprising
a first housing barrel,
a second housing barrel normally freely rotatable in said first barrel,
a motor carried by one of said barrels,
a rotatable chuck carried by the other of said barrels,
means for transmitting rotation between said motor and said chuck,
normally ineffective chuck control means responsive to relative rotation of said barrels in one direction to close said chuck and responsive to relative rotation of said barrels in the opposite direction to open said chuck, and
manually controlled means on one of said barrels for selectively rendering said chuck control means effective.

12. A dental handpiece comprising
a first housing barrel,
a second housing barrel rotatably mounted adjacent one end thereof in said first barrel,
a rotatable chuck having spring prongs at one end thereof for gripping a workpiece,
said prongs being adjacent the opposite end of said second barrel,
a first bearing rotatably supporting said chuck adjacent the opposite end thereof in said second barrel,
a chuck sleeve supporting said chuck adjacent said opposite end of said second barrel,
said sleeve being movable endwise over said chuck to engage said prongs whereby to close said prongs,
a second bearing slideably and rotatably supporting said sleeve in said second barrel adjacent said opposite end of said second barrel, spring means intermediate said first bearing and said sleeve for moving said sleeve endwise in one direction to close said prongs, and means responsive to relative rotation of said barrels for moving said chuck sleeve in the opposite direction to cause said prongs to open.

13. A dental handpiece comprising a rotatable chuck, a fluid operated vane motor for rotating said chuck, said motor comprising a stator having a cylindrical bore therein, a rotor, means connecting said rotor to said chuck, a bearing supporting said rotor in said bore for rotation about an axis eccentric to the axis of said bore, diametrically opposed radially extending slots in said rotor, vanes in said slots engageable with the surface of said bore, means for admitting fluid under pressure into said bore to rotate said rotor, and means connecting said vanes to move radially in unison in said slots.

14. A dental handpiece as defined in claim 13 wherein said last mentioned means comprises spaced connector elements integrally connecting said vanes to move radially in unison in said slots.

15. A dental handpiece as defined in claim 14 comprising means in said rotor forming slide bearings for said connector elements.

* * * * *